(12) United States Patent
Orr et al.

(10) Patent No.: US 6,968,741 B2
(45) Date of Patent: Nov. 29, 2005

(54) PORTABLE PRESSURE TRANSDUCER, PNEUMOTACH FOR USE THEREWITH, AND ASSOCIATED METHODS

(75) Inventors: Joseph A. Orr, Park City, UT (US); Scott A. Kofoed, Salt Lake City, UT (US); Kevin Durst, Salt Lake City, UT (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 10/729,404

(22) Filed: Dec. 5, 2003

(65) Prior Publication Data

US 2004/0118212 A1    Jun. 24, 2004

Related U.S. Application Data

(62) Division of application No. 10/139,920, filed on May 7, 2002, now Pat. No. 6,691,579.

(60) Provisional application No. 60/289,540, filed on May 7, 2001.

(51) Int. Cl.$^7$ ................................................. G01L 7/00
(52) U.S. Cl. ............................. 73/700; 73/753; 73/756
(58) Field of Search ..................... 73/700–756, 861.42, 73/861.52, 861.61, 861.63, 861.65

(56) References Cited

U.S. PATENT DOCUMENTS

| | | | |
|---|---|---|---|
| 3,815,411 A | 6/1974 | Emerson | |
| 4,859,858 A | 8/1989 | Knodle et al. | |
| 4,859,859 A | 8/1989 | Knodle et al. | |
| 5,029,591 A * | 7/1991 | Teves | 600/528 |
| 5,042,522 A * | 8/1991 | Corenman et al. | 137/239 |
| 5,098,384 A | 3/1992 | Abrams | |
| 5,153,436 A | 10/1992 | Apperson et al. | |
| 5,379,650 A | 1/1995 | Kofoed et al. | |
| 5,722,417 A | 3/1998 | Garbe | |
| 5,789,660 A | 8/1998 | Kofoed et al. | |
| 5,906,204 A | 5/1999 | Beran et al. | |
| 6,312,389 B1 | 11/2001 | Kofoed et al. | |
| 6,325,978 B1 | 12/2001 | Labuda et al. | |
| 6,585,662 B1 * | 7/2003 | Jones et al. | 600/538 |

* cited by examiner

*Primary Examiner*—Edward Lefkowitz
*Assistant Examiner*—Jermaine Jenkins
(74) *Attorney, Agent, or Firm*—Michael W. Haas

(57) ABSTRACT

A system for sensing respiratory pressure includes a portable pressure transducer configured to be carried by or proximate to a respiratory conduit, such as a breathing circuit or a nasal canula. The portable pressure transducer may removably couple with a pneumotach, in the form of an airway adapter, disposed along the respiratory conduit. The pneumotach may include two pressure ports positioned at opposite sides of an obstruction, which partially blocks flow through a primary conduit of the pneumotach. Corresponding sample conduits of the portable pressure transducer removably couple with the pressure ports. The pressure ports may have sealing elements which are configured to seal against piercing members of the sample conduits upon introduction of the piercing members therethrough. Upon removal of the piercing members, the sealing elements substantially reseal. Methods for using the system are also disclosed.

15 Claims, 6 Drawing Sheets

PORTABLE PRESSURE TRANSDUCER, PNEUMOTACH FOR USE THEREWITH, AND ASSOCIATED METHODS

CROSS-REFERENCE TO RELATED APPLICATION

This application is a Divisional of U.S. patent application Ser. No. 10/139,920 filed May 7, 2002, now U.S. Pat. No. 6,691,579 which claims the benefit under the provisions of 35 U.S.C. § 119(e) of U.S. provisional application No. 60/289,540, filed on May 7, 2001.

BACKGROUND OF THE INVENTION

1. Field of the Invention

The present invention relates generally to apparatus for measuring respiratory pressure or flow and, more specifically, to respiratory pressure transducers. More particularly, the present invention relates to pressure transducers which may be positioned proximate to a respiratory conduit which is configured to communicate with the airway of an individual.

2. Background of Related Art

Respiratory flow measurement during the administration of anesthesia, in intensive care environments, and in monitoring the physical condition of athletes and other individuals prior to and during the course of training programs and other medical tests provides valuable information for assessment of cardiopulmonary function and breathing circuit integrity. Many different technologies have been applied to create a flow meter that attempts to meet the demanding requirements of these environments.

Although various other types of pressure measurement apparatus are known, differential pressure flow meters have conventionally been used to obtain respiratory flow measurements. While pressure monitoring is typically performed to measure delivered (i.e., inspired) and exhaled volume by monitoring respiratory mechanics parameters, such as airway pressures, flow rates, and breath volumes, clinicians can better provide quality health care to patients requiring breathing assistance. Additionally, pressure monitoring may be used in conjunction with respiratory gas measurements to assess other respiratory parameters, such as oxygen consumption, carbon dioxide elimination, and even cardiac output or pulmonary capillary blood flow.

Differential pressure flow meters operate on the basis of Bernoulli's principle: the pressure drop across a restriction is proportional to the volumetric flow rate of the air. The relationship between flow and the pressure drop across a restriction or other resistance to flow is dependent upon the design of the resistance. In some differential pressure flow meters, which are commonly termed "pneumotachs", the flow restriction has been designed to create a linear relationship between flow and a pressure differential. Such designs include the Fleisch pneumotach, in which the restriction is comprised of many small tubes or a fine screen to ensure laminar flow and a more linear response to flow. Another physical configuration is a flow restriction having an orifice that varies in relation to the flow. Such designs include the variable orifice, fixed orifice and venturi-type flow meters. Exemplary patents for variable orifice differential pressure flow sensors include U.S. Pat. No. 4,993,269, issued to Guillaume et al. on Feb. 19, 1991, U.S. Pat. No. 5,038,621, issued to Stupecky on Aug. 13, 1991, U.S. Pat. No. 5,763,792, issued to Kullik on Jun. 9, 1998, and U.S. Pat. No. 5,970,801, issued to Ciobanu on Oct. 26, 1999. Exemplary patents for fixed orifice differential pressure flow-sensors include U.S. Pat. No. 5,379,650, issued to Kofoed et al. on Jan. 10, 1995, U.S. Pat. No. 5,925,831, issued to Storsved on Jul. 20, 1999, and U.S. Pat. No. 6,203,502, issued to Hilgendorf on Mar. 20, 2001.

Many known differential pressure flow sensors suffer deficiencies when exposed to less than ideal gas and flow inlet conditions and, further, possess inherent design problems with respect to their ability to sense differential pressure in a meaningful, accurate, repeatable manner over a substantially dynamic flow range. This is particularly true when the flow sensor is needed to reliably and accurately measure low flow rates, such as the respiratory flow rates of infants. Proximal flow measured at the patient's airway can be substantially different from flow measured inside or at the ventilator. Many ventilators measure flow, not at the proximal airway, but close to the ventilator. Measurements of flow in this way may result in a substantial difference between the flow, pressure, and volume of gases that are delivered to or exhaled by the patient and that are reported by a pressure or flow sensor which is associated with the ventilator. At least a portion of this discrepancy is because of wasted compression volume, which distends and may elongate a length of respiratory conduit positioned between the patient's airway and the pressure or flow sensor, and humidification or dehumidification attributable to the length of the respiratory conduit between the patient's airway and the pressure or flow sensor. As the compliance of the respiratory conduit may be a known value, some ventilator manufacturers apply a correction for the wasted compression volume. Even when a correction is applied, precise estimation of the wasted and inhaled portions of the compression volume is difficult because of variations between individual respiratory conduits, the use of humidifiers, the use of heat-moisture exchangers, and other circuit components. Within a typical respiratory conduit, gas conditions (e.g., temperature, pressure, humidity, etc.) may vary considerably, depending upon the distance of the gases from the airway of the monitored individual. As gas conditions nearest the individual are most likely to reflect the corresponding conditions within the individual's airway, the preferred location for monitoring inspiratory and expiratory flows from a patient in the critical care environment is proximal (i.e., as close to the individual's airway as possible).

Routine clinical use of differential flow meters has increased significantly in the last few years with the development of more robust designs, such as that disclosed in U.S. Pat. No. 5,379,650, issued to Kofoed et al. on Jan. 10, 1995 (hereinafter "the '650 Patent"), the disclosure of which is hereby incorporated herein in its entirety by this reference. The differential flow meter described in the '650 Patent, which has overcome the majority of the problems that were previously encountered when prior differential pressure flow sensors were used, includes a tubular housing containing a diametrically oriented, longitudinally extending strut. The strut of the flow sensor disclosed in the '650 Patent includes first and second lumens with longitudinally-spaced pressure ports that open into respective axially located notches formed at each end of the strut.

Despite such improvements in the performance of differential pressure flow meters, differential pressure flow meters continue to include a pneumotach positioned along a respiratory conduit, a typically remotely positioned pressure monitor, and tubing that operatively connects the pneumotach and the pressure monitor with one another. The tubing transmits pressure at each port of the pneumotach to one or more pressure sensors that are contained within the monitor.

Typically, several feet of flexible, small bore, dual or triple lumen tubing are used to connect the pneumotach and the pressure monitor to one another.

The use of such small bore tubing is, however, somewhat undesirable from the standpoint that the pressure samples which are conveyed from the pneumotach may be damped or distorted as they travel through the tubing. Consequently, it is often necessary to screen the sensors and individually balance the internal pneumatics of the monitor to ensure accurate measurement of airway pressure and, thus, to provide an acceptable level of clinical performance under conditions such as those typically encountered with monitored patients (i.e., low ventilatory compliance).

Additionally, the use of flow sensors with tubing in clinical environments, such as critical and intensive care where high humidity is often the norm, leads to the condensation of moisture in the pressure transmission tubing, whether or not the pressure transmission tubing or any portion of the respiratory conduit is heated. One result of condensation is a damping and distortion of respiratory samples, or the pressure "signals", that propagate down the pressure transmission tubes. Typically, pressure transmission tubes are periodically purged with air from a compressed gas source or a pump in order to reduce the adverse effects of condensate on pressure and flow measurements, which creates additional work for healthcare personnel and, therefore, is a somewhat undesirable practice. Additionally, accidental or intentional disconnection of the tubing from the monitor may cause condensate or even sputum to flow into the pressure transmission tubes and potentially contaminate the monitor.

Further, the lengthy tubing of conventional differential pressure flow sensors is typically discarded after use, resulting in a significant amount of plastic waste. Accordingly, employing such tubing as a single-use element of a differential pressure flow sensor is costly.

Reuse of pressure transmission tubing is also typically contrary to manufacturer recommendations due to the potential for contamination of the pressure transducer, as well as the potential (although not significant) extubation hazard posed thereby in the clinical environment. Nonetheless, such tubing is often reused, particularly outside of the United States, as a cost-saving measure.

The inventors are not aware of a differential pressure flow sensor that lacks pressure transmission tubes extending between the pneumotach and monitor thereof, or of a differential flow sensor that includes a transducer, that is configured to be carried upon a respiratory conduit that communicates with the airway of an individual.

SUMMARY OF THE INVENTION

The present invention includes a portable pressure transducer which is configured to be positioned on or proximate to a respiratory conduit that is, in turn, configured to communicate with the airway of an individual. The present invention also includes a pneumotach with which the portable pressure transducer may be coupled to facilitate communication between the individual's airway and the portable pressure transducer. When the portable pressure transducer and pneumotach are assembled with one another, respiratory gas samples may be transported from the respiratory conduit to the portable pressure transducer while maintaining a fluid-tight seal between the portable pressure transducer and the pneumotach. In addition, the present invention includes methods for obtaining measurements of respiratory pressures, flows, volumes, and other respiratory and blood gas parameters.

A pneumotach that incorporates teachings of the present invention may be embodied as a so-called "airway adapter" and includes a primary conduit, which aligns with the primary pathway through a respiratory conduit, such as a breathing circuit or a nasal canula, that is configured to communicate with the airway of an individual. In addition to the primary conduit, the pneumotach includes two pressure ports that communicate with the primary conduit and that are positioned at opposite sides of an obstruction located along and partially blocking the primary conduit, as well as other components that are typically associated with pressure or flow sensing apparatus. The pressure ports are configured to communicate with sample conduits of a portable pressure transducer upon coupling of the portable pressure transducer to the pneumotach. The location of each pressure port to which the sample conduits couple may include a resealing material or a so-called "self-healing" material, which seals the pressure ports prior to coupling of the sample conduits of the portable pressure transducer thereto and reseals upon uncoupling of the sample conduits of the portable pressure transducer from the pressure ports of the pneumotach.

The pneumotach may optionally include additional functionality, such as for monitoring the amounts of one or more gases or vaporized substances in the respiration of an individual. By way of example only, the pneumotach may include one or more windows and be configured to have an optical transducer of an infrared sensor or a luminescence-quenching type sensor coupled thereto.

A portable pressure transducer according to the present invention is configured to be operatively coupled to a pneumotach of the invention and, thus, may be carried upon a respiratory conduit. Either the pressure ports of the pneumotach or those of the sample conduits of the portable pressure transducer are substantially larger than the other so as to facilitate the formation and maintenance of a fluid-tight (e.g., airtight) seal without requiring precise alignment between all (typically two) of the pressure ports and their corresponding sample conduits. By configuring the pneumotach in this manner, wide manufacturing tolerances may be used, which decreases the cost of the pneumotach, thereby making the pneumotach more amenable to single patient use (i.e., disposability). Further, configuring one of the pneumotach and the portable pressure transducer with relatively loose tolerances facilitates the relatively easy assembly of these two structures. In addition to sample conduits that align with the pressure ports of the pneumotach, the portable pressure transducer may include valves that direct the flow of an individual's respiration therethrough and also includes one or more pressure sensors by which an individual's respiratory pressure is measured.

Respiratory measurements obtained with a respiratory monitoring system that includes a pneumotach and a portable pressure transducer according to the present invention may be used, as known in the art to determine various pressure and flow parameters relating to the respiration of an individual, as well as other respiratory profile parameters that are based in part on the pressure or flow of the individual's respiration. Accordingly, methods of using the pneumotach and portable pressure transducer of the present invention are also within the scope thereof.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which depict various aspects of exemplary embodiments of the present invention.

DETAILED DESCRIPTION

Figure 1:
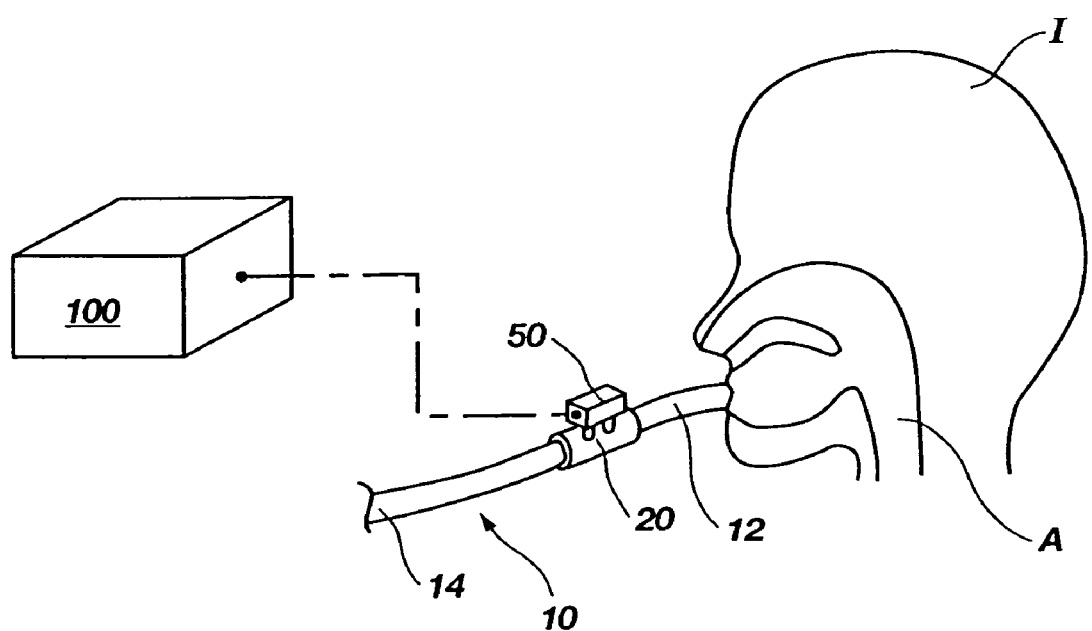
FIG. 1 is a schematic representation of a respiratory conduit that communicates with an airway of an individual and which has a pneumotach and portable pressure transducer of the present invention operatively coupled thereto.

With reference to FIG. 1, a respiratory conduit 10 is depicted. Respiratory conduit 10 may comprise a breathing circuit which includes an endotracheal tube, a nasal canula, or any other conduit that is configured to communicate with the airway A of an individual I. As depicted, one end 12 of respiratory conduit 10 is placed in communication with airway A, while the other end 14 of respiratory conduit 10 opens to the atmosphere, a source of gas to be inhaled by individual I, or a ventilator, as known in the art. Positioned along its length, respiratory conduit 10 includes at least one airway adapter, in this case a pneumotach 20, which is a component of a type of pressure sensor. Also shown in FIG. 1 is a portable pressure transducer 50 coupled with and in flow communication with pneumotach 20. Portable pressure transducer 50 may, in turn, communicate electronically with a computer, such as a pressure or flow monitor 100, as known in the art.

Figure 2:
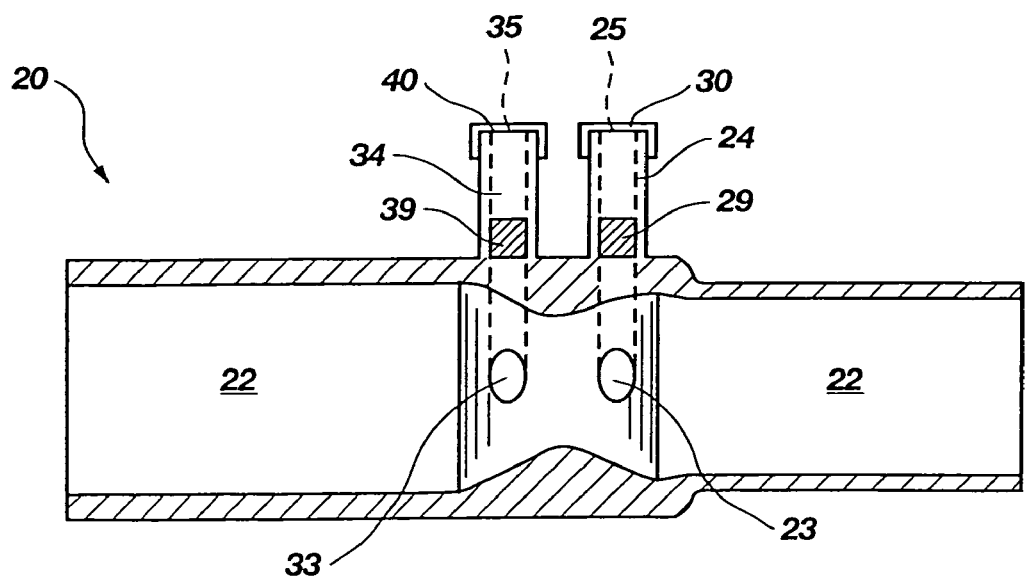
FIG. 2 is a cross-sectional representation of an exemplary embodiment of a pneumotach, in the form of an airway adapter, that incorporates teachings of the present invention.

Referring now to FIG. 2, the various features of pneumotach 20 may be configured as known in the art, for example, like the corresponding features of the differential flow sensors that are described in the '650 Patent. Among other things, pneumotach 20 includes a primary conduit 22 and two pressure ports 24 and 34 that are in flow communication with primary conduit 22 through apertures 23 and 33. Also, pneumotach 20 includes an obstruction 21 to block a portion of the flow of respiration or other gases or gas mixtures along the path of primary conduit 22 and positioned at least partially between pressure port 24 and pressure port 34 to create a pressure differential in the gas flow therebetween. Pneumotach 20 may be formed from an inexpensive, readily mass-producible material, such as an injection moldable plastic, so that pneumotach 20 may be marketed as a disposable unit.

Figure 4:
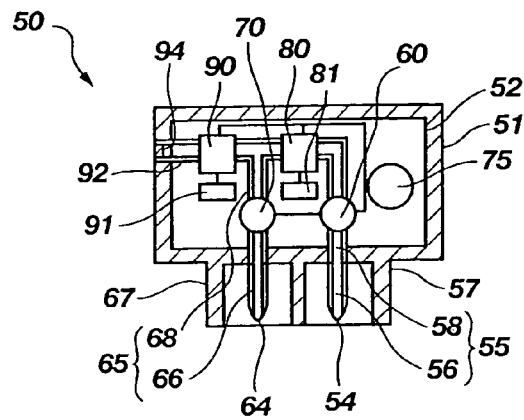
FIG. 4 is a cross-sectional representation of an exemplary embodiment of a portable pressure transducer according to the present invention, which is configured to be assembled with the pneumotach shown in FIG. 2.
Figure 5:
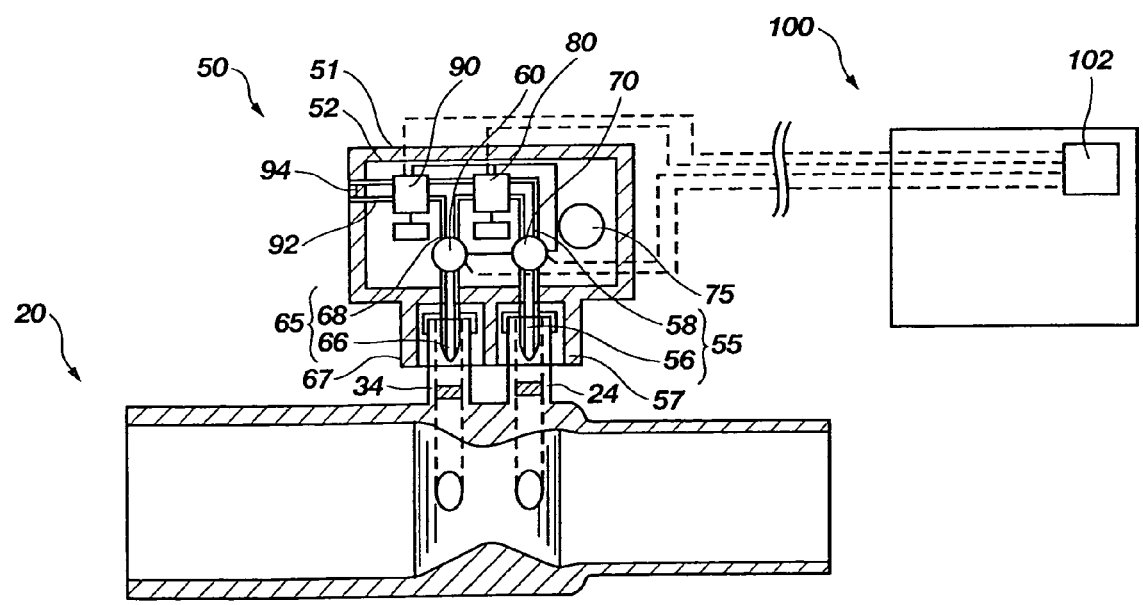
FIG. 5 is a side cross-sectional assembly view of the pneumotach of FIG. 2 assembled with the portable pressure transducer of FIG. 4.

Pneumotach 20 is different from the pneumotachs described in the '650 Patent in that, rather than being configured to be coupled to elongate, flexible conduits, or pressure transmission tubes, that transport respiratory samples to a remotely located pressure transducer for evaluation, pressure ports 24 and 34 are configured to be coupled to a remotely located pressure transducer for evaluation, pressure ports 24 and 34 are configured to be coupled directly to corresponding sample ports 54 and 64, respectively, of a complementarily configured pressure transducer 50 (See FIGS. 4 and 5).

As an example, each pressure port 24, 34 may have a sealing element 30, 40 covering an opening 25, 35 of that pressure port 24, 34. As an example and not to limit the scope of the present invention, each sealing element 30, 40 may comprise a film formed from a material, such as latex, silicone, or the like, that may be pierced by a member (e.g. a needle) and maintain a seal at a pressure of up to about 150 cm $H_2O$ around the piercing member. Also, the material of each sealing element 30, 40 may be formulated to reseal following the removal of a piercing member therefrom.

Sealing elements 30 and 40 may also hold filters 29 and 39 within respective pressure ports 24 and 34 of pneumotach 20. Filters 29 and 39 may be positioned within their respective pressure ports 24 and 34 in such a way as to avoid disruption (e.g. piercing, tearing, etc.) thereof when a complementarily configure pressure or flow transducer (e.g. portable pressure transducer 50 shown in FIGS. 4 and 5) having the aformentioned piercing members is coupled to pneumotach 20. Filters 29 and 39 may prevent contamination (e.g. by particulates, moisture, microorganisms, etc.) of a pressure or flow transducer upon coupling of the same to pneumotach 20. By preventing contamination of the pressure or flow transducer, filters 29 and 39 facilitate reuse of the pressure or flow transducer without requiring substantial cleaning or sterilization thereof between uses. Accordingly, a pressure or flow transducer that is complementary to pneumotach 20 may be used with multiple patents. Filters 29 and 39 may comprise any suitable filter medium that will facilitate accurate transmission of a pressure waveform from pressure ports 24 and 34 into a complementary pressure transducer. Suitable media for filters 29 and 39 include, without limitation, hydrophobic, antimicrobial filter materials, such as those typically employed in respiratory conduits, which may be in the form of felt, particles, or otherwise, as known in the art. While it is desirable that filters 29 and 39 not substantially restrict the flow of sampled respiratory gases through pressure ports 24 and 34, same resistance to airflow is allowable, so long as a sufficient differential pressure may be communicated from pressure ports 24 and 34 of pneumotach 20 to a complementarily configured pressure or flow transducer.

Sealing elements 30 and 40 may be secured to their corresponding pressure ports 24 and 34, respectively, by any suitable retention means. By way of example only, an adhesive material which is compatible with the materials from which both sealing elements 30 and 40 and pressure ports 24 and 34 are formed may be placed in appropriate locations to sealingly secure sealing elements 30 and 40 to their corresponding pressure ports 24 and 34.

Figure 3:
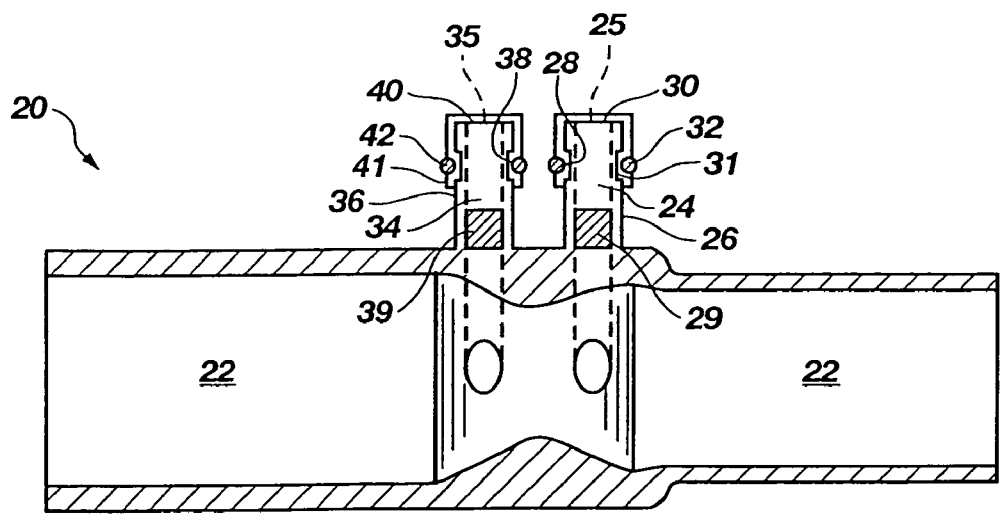
FIG. 3 is a cross-sectional representation of a variation of the pneumotach depicted in FIG. 2.

Alternately, as depicted in FIG 3, mechanical retention means, such as the illustrated rings 32 and 42, may be used to secure sealing elements 30 and 40 to their corresponding pressure ports 24 and 34. Each ring 32, 42 is configured to be positioned peripherally (or, as illustrated, circumferentially) around its corresponding pressure port 24, 34. When positioned around a corresponding portion of a pressure port 24, 34, little or no clearance exists between each ring 32, 42 and an adjacent outer surface 26, 36 of the corresponding pressure port 24, 34. Once sealing elements 30 and 40 are appropriately positioned over their respective openings 25 and 35 of pressure ports 24 and 34, respectively, a ring 32, 42 (which may be formed from heat-shrinkable material) or other mechanical retention means may be positioned around its corresponding pressure port 24, 34 and a peripheral portion 31, 41 of the corresponding sealing element 30, 40 thereon. In this fashion, rings 32 and 42 hold peripheral portions 31 and 41 of the respective sealing members 30 and 40 in place. As depicted, an outer surface 26, 36 of each pressure port 24, 34 may include a peripheral groove 28, 38 formed therein, which is configured to receive at least a portion of a corresponding ring 32, 42, as well as a peripheral portion 31, 41 of a sealing element 30, 40 positioned between the ring 32, 42 and outer surface 26, 36 of pressure port 24, 34.

Turning now to FIGS. 4 and 5, a portable pressure transducer 50 that incorporates teachings of the present invention is illustrated. Portable pressure transducer 50 is configured to be at least temporarily coupled to a complementarily configured airway adapter that senses respiratory pressure or flow, such as pneumotach 20.

Portable pressure transducer 50 includes sample ports 54 and 64, which are positioned in laterally adjacent, spaced apart relation to one another. The distance at which sample ports 54 and 64 are spaced apart from one another, as well as their relative orientations, may facilitate communication with corresponding pressure ports 24 and 34 of pneumotach 20 when portable pressure transducer 50 and pneumotach 20 are assembled with one another. As depicted, sample ports 54 and 64 are each formed at respective coupling ends 56 and 66 of sample conduits 55 and 65 of portable pressure transducer 50. Coupling ends 56 and 66 of sample conduits 55 and 65 protrude from an outer surface 51 of a housing 52 of portable pressure transducer 50, while internal portions 58 and 68 of sample conduits 55 and 65, respectively, are located within housing 52.

In the illustrated example, which in no way limits the scope of the present invention, each coupling end 56, 66 of a sample conduit 55, 65 comprises a hollow needle, such as an 18, 20, or 25 gauge injection type needle. When a needle is employed as coupling end 56, 66, a smaller circumference (i.e., higher gauge number) may cause less damage to a sealing element 30, 40 through which an end of the needle is inserted, which may better facilitate healing or resealing of sealing element 30, 40 following removal of the needle of coupling end 56, 66 therefrom. Additionally, if the outer diameter of each coupling end 56, 66 is smaller than the inner diameter of its corresponding pressure port 24, 34, precise alignment of coupling ends 56 and 66 with their corresponding pressure ports 24 and 34 may not be required. The needle of each coupling end 56, 66 is sealingly coupled to a corresponding internal portion 58, 68 of sample conduit 55, 65 in such a way as to withstand, without substantially leaking, the pressures to which differential pressure transducer 50 will be exposed (e.g., pressures of up to about 150 mm Hg).

Housing 52 of portable pressure transducer 50 may include protective sleeves 57 and 67 that may extend therefrom and circumferentially surround coupling ends 56 and 66, respectively, of sample conduits 55 and 65 along substantially their entire external lengths. Protective sleeves 57 and 67 may also extend beyond their respective coupling ends 56 and 66 of sample conduits 55 and 65, respectively, so as to prevent coupling ends 56 and 66 from contacting and, when needles are used, from scratching or puncturing other structures, the individual being monitored, or healthcare personnel working with or near portable pressure transducer 50. Protective sleeves 57 and 67 are also configured to receive at least a portion of pressure ports 24 and 34 that correspond to sample ports 54 and 64, respectively.

Internal portions 58 and 68 of sample conduits 55 and 65 independently communicate respiratory gases to a differential pressure sensor 80 located within housing 52 of portable pressure transducer 50. Differential pressure sensor 80 senses a pressure differential across at least a portion of obstruction 21 and transmitted from the airway A of an individual I (FIG. 1) by pressure ports 24 and 34 and their corresponding sample conduits 55 and 65, respectively. As differential pressure sensor 80 is in communication with both sample conduits 55 and 65, it is capable of measuring a pressure drop across an element, such as obstruction 21 positioned in the path of primary conduit 22 of pneumotach 20 and between pressure ports 24 and 34 with which sample conduits 55 and 65 respectively communicate. As portable pressure transducer 50 is to be coupled with a pneumotach 20 which is, in turn, configured to be secured to a respiratory conduit 10 (FIG. 1), it may be desirable for a differential pressure sensor 80 thereof to be of a design insensitive to tilting, vibration, movement, or any combination thereof. It may also be desirable for differential pressure sensor 80 to be insensitive to, or capable of compensating for common mode pressure variations within the respiratory conduit. By way of example and not to limit the scope of the present invention, differential pressure sensor 80 may be configured to measure pressure differences of up to about 4 in. $H_2O$ (i.e., about 10 cm $H_2O$), although a differential pressure sensor 80 of portable pressure transducer 50 of the present invention maybe of a type capable of measuring pressure differences of up to about 10 in. $H_2O$ (i.e., about 25 cm $H_2O$). By way of example only, a dual chip pressure transducer, which includes a bridge circuit array of resistors and which is capable of monitoring both airway and differential pressure, may be used as differential pressure sensor 80 of portable pressure transducer 50. An example of such a dual chip pressure transducer is the XCX Series transducer manufactured by AllSensors Corporation of San Jose, Calif.

Differential pressure sensor 80 may communicate signals that are representative of the measured difference in pressure between air or gases within sample conduit 55 and air or gases within sample conduit 65 to a processor 102 of a pressure or flow monitor 100, as known in the art (e.g., along a computer communication cable, by wireless transmission, such as infrared transmission, etc.). Processor 102, under control of one or more programs in the form of software or firmware, may then, based on the signals received thereby, employ known principles and algorithms to calculate respiratory flow. Signal conditioning electronics 81 of a type known in the art, such as an instrumentation amplifier, may be associated with differential pressure sensor 80, as known in the art, to amplify the signals that are generated and transmitted thereby as well as reduce or eliminate noise and other signal artifacts. Processor 102 may also quantify airway pressure at different points or portions of the monitored individual's respiration, also by known processes.

Sample conduit 55 also communicates with a gauge or ambient pressure sensor 90, which is also in flow communication with the atmosphere external to portable pressure transducer 50. Gauge pressure sensor 90 may be positioned proximally, in reference to the location of the monitored individual, relative to differential pressure sensor 80. In the illustrated example, gauge pressure sensor 90 communicates with the atmosphere by way of a conduit 92 that extends through housing 52 of portable pressure transducer 50 and that opens to the atmosphere. As gauge pressure sensor 90 communicates with both the atmosphere (e.g., by way of conduit 92) and the airway A (FIG. 1) of an individual I (by way of sample conduit 55, as well as other conduits and ports), gauge pressure sensor 90, which may also comprise a differential pressure sensor, may sense differences between atmospheric pressure and airway pressure. Gauge pressure sensor 90 may be of a type insensitive to one or more of tilt, vibration, movement, or any combination thereof. It may also be desirable for gauge pressure sensor 90 to be insensitive to, or capable of, compensating for common mode pressure variations within the respiratory conduit. As an example and not by way of limitation, gauge pressure sensor 90 may be capable of sensing pressure differences of up to about 120 mm Hg. By way of example only, an XCX Series, dual chip differential pressure sensor available from AllSensors may be used as gauge pressure sensor 90.

Gauge pressure sensor 90 generates signals representative of such measured pressure and communicates the same to processor 102, which may be programmed, as known in the art, to consider the differences between atmospheric and airway pressure in quantifying the pressure at one or more particular points or portions of the monitored individual's respiration, as well as in calculating respiratory flow. These signals may be amplified or otherwise modified by signal conditioning electronics 91, such as an instrumentation amplifier, which is associated with gauge pressure sensor 90 in a manner known in the art.

Portable pressure transducer 50 may also include a valve 60, 70 positioned along each sample conduit 55, 65, between coupling end 56, 66 thereof and differential pressure sensor 80 and/or gauge pressure sensor 90 (i.e., upstream from sensors 80 and/or 90). Each valve 60, 70 controls (i.e., permits or restricts) the flow of respiratory gases through its corresponding sample conduit 55, 65. For example, when valves 60 and 70 are both in open positions, respiratory gases may flow therethrough and, thus, along their respective sample conduits 55 and 65. Conversely, when valves 60 and 70 are closed, respiratory gases are restricted from flowing completely through sample conduits 55 and 65. Exemplary valves that may be used in portable pressure transducer 50 include the three-way solenoid valves marketed under the trade name X-VALVE® by the Pneutronics Division of Parker Hannifin Corporation, which is located in Hollis, N.H., or titanium nickel valves manufactured by TiNi Alloy Company of San Leandro, Calif. Valves 60 and 70 may be configured to communicate with a control device, such as processor 102 of monitor 100 or a processor of a separate computer (not shown) associated with monitor 100, which is programmed to actuate valves 60 and 70 and, thus, to control the flow of respiratory gases through sample conduits 55 and 65. Such communication may be effected wirelessly (e.g., by infrared signals or other known, suitable wavelengths of electromagnetic radiation) or via wires or cables.

Valves 60 and 70 may be closed, or placed in a "zeroing" position, to facilitate the measurement of atmospheric pressure only and, thus, permit gauge pressure sensor 90 and differential pressure sensor 80 to generate so-called "baseline" pressure signals. Accordingly, by periodically reestablishing baseline pressure, any susceptibility that differential pressure sensor 80 or gauge pressure sensor 90 may exhibit to experiencing "baseline drift " may be counteracted.

Alternately, when valves 60 and 70 are both in open, or "measuring," positions, respiratory samples may flow through sample conduits 55 and 65 and to differential pressure sensor 80 and gauge pressure sensor 90, thereby facilitating measurement of airway pressure. The pressure measurements that are obtained with valves 55 and 65 in open positions may be corrected by considering the baseline pressure measured by each of differential pressure sensor 80 and gauge pressure sensor 90. For example, the baseline pressure of each sensor 80, 90 may be subtracted from the pressure measurement subsequently obtained by that sensor 80, 90.

Portable pressure transducer 50 may also include a power provision element 75, such as an interconnection (e.g., a wire or cable) to a remote power source or an internal power source (e.g., a battery) for supplying power to valves 60 and 70, differential pressure sensor 80, gauge pressure sensor 90, and other power-consuming elements of portable pressure transducer 50.

Housing 52 of portable pressure transducer 50 may be configured to prevent moisture-sensitive components thereof, such as differential pressure sensor 80 and gauge pressure sensor 90, from being exposed to moisture (e.g., from humidity, sources of fluid, etc.). In addition, filters 29 and 39 of pneumotach 20 may prevent moisture from coming into contact with these moisture-sensitive components of portable pressure transducer 50. A similar, optional filter 94 may likewise be positioned along conduit 92 to prevent exposure of gauge pressure sensor 90 to moisture from the environment external to housing 52.

Figure 5A:
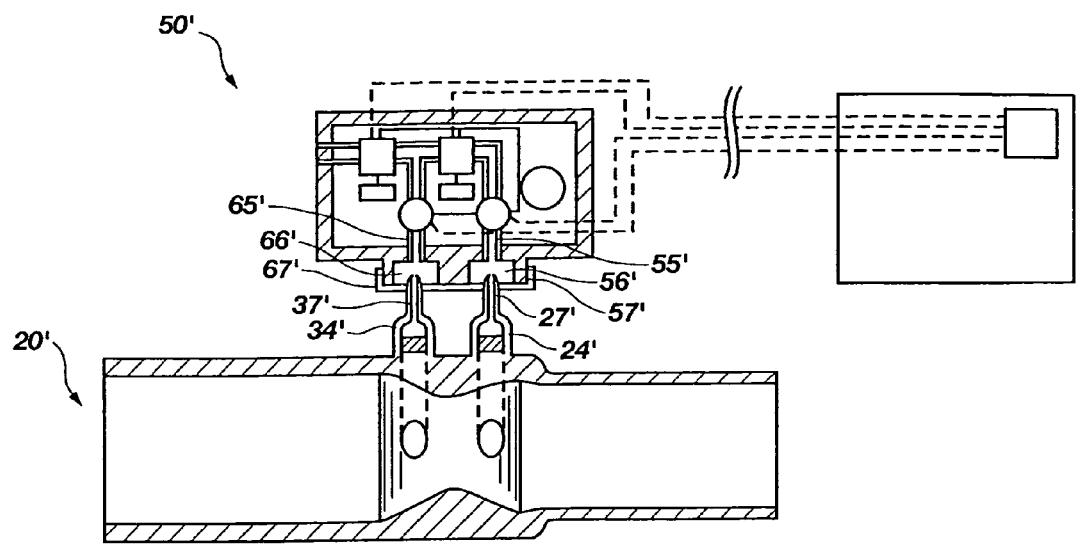
FIG. 5A is a side cross-sectional assembly view of another embodiment of pneumotach and complementary portable pressure transducer according to the present invention.

As an alternative to the embodiments of pneumotach 20 and portable pressure transducer 50 shown in and described with reference to FIGS. 2–5, various features of the pressure ports of the pneumotach and of the coupling ends of the sample conduits of the portable pressure transducer may be reversed, as depicted in FIG. 5A. As shown, a pneumotach 20' may include pressure ports 24' and 34' with hollow needles 27' and 37' protruding therefrom. Needles 27' and 37' are configured to be coupled with coupling ends 56' and 66', respectively, of corresponding sample conduits 55' and 65' of a complementarily configured portable pressure transducer 50'. In particular, as the outer diameter of each needle 27', 37' is significantly smaller than the inner diameter of a coupling end 56', 66' of its corresponding sample conduit 55', 65' over which a protective sleeve 57', 67', or sealing element, is positioned, each needle 27', 37' is configured to roughly align with and temporarily puncture a sealing element 57', 67' on a coupling end 56', 66' of its corresponding sample conduit 55', 65'. Needles 27' and 37' may comprise any hollow, injection-type needle with a small circumference (e.g., an 18, 20, or 25 gauge needle) and a tip which will readily pierce sealing element 57', 67'. Sealing elements 57' and 67' may be formed from any material that will form an adequate seal (e.g., a seal which may be maintained at pressures of up to about 150 mm Hg) around the outer surface of a needle 27', 37', while substantially resealing upon removal of a needle 27', 37' therefrom. Exemplary materials that may be used as sealing elements 57' and 67' include, without limitation, films of latex, silicon, and other relatively soft, resilient elastomeric materials.

Figure 6:
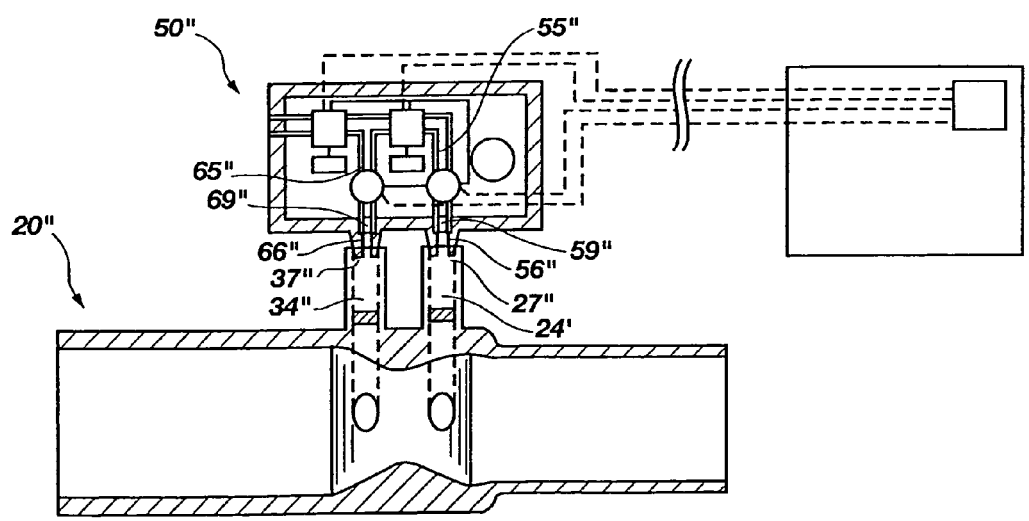
FIG. 6 is a side cross-sectional assembly view of another exemplary embodiment of portable pressure transducer and complementary airway adapter type pneumotach according to the present invention.

In another exemplary embodiment of both a pneumotach and portable pressure transducer that incorporate teachings of the present invention, corresponding elements of these apparatus are configured to matingly engage one another upon assembly of the pneumotach and portable pressure transducer with one another. These embodiments of pneumotach 20" and portable pressure transducer 50", which are depicted in FIG. 6, require more precise, or finer, alignment between corresponding features than do the previously described embodiments.

Pneumotach 20" differs from pneumotach 20 (FIGS. 2, 3, and 5) in that pressure ports 24" and 34" thereof include coupling ends 27" and 37" (female members in the depicted example) that are configured to matingly engage (e.g., by way of an interference fit, complementary threaded joints (not shown), or otherwise) complementary coupling ends 56" and 66" (male members in the depicted example) of corresponding sample conduits 55" and 65", respectively, of portable pressure transducer 50". A filter 29", 39" extends across each pressure port 24", 34" to prevent microorganisms, moisture, and other contaminants from passing therethrough and into sample conduits 55" and 65" of portable pressure transducer 50". Sample conduits 55" and 65" may likewise have filters 59" and 69" extending thereacross to prevent contamination of the other elements of portable pressure transducer 50". Filters 29", 39", 59", and 69" may each comprise any suitable filter medium that will facilitate accurate transmission of a pressure waveform from pressure ports 24" and 34" into corresponding sample conduits 55" and 65", respectively. Suitable media for filters 29", 39", 59", and 69" include, without limitation, hydrophobic, antimicrobial filter materials, such as those typically employed in respiratory conduits, which may be in the form of felt, particles, or otherwise, as known in the art. Other features of pneumotach 20" and portable pressure transducer 50" are substantially the same as those which are described above with respect to pneumotach 20, in reference to FIGS. 2, 3, and 5, and portable pressure transducer 50, in reference to FIGS. 4 and 5.

Optionally, an airway adapter and complementary transducer that incorporate teachings of the present invention may be configured for multiple diagnostic functions. By way of example only, in addition to functioning as a pneumotach, an airway adapter of the present invention may also include a material sensing element, such as one or both of an infrared sensor, as described in the U.S. Pat. Nos. 4,859,858 and 4,859,859, both of which issued to Knodle et al. on Aug. 22, 1989 (hereinafter respectively "the '858 Patent" and "the '859 Patent"), and U.S. Pat. No. 5,153,436, issued to Apperson et al. on Oct. 6, 1992 (hereinafter "the '436 Patent"), the disclosures of each of which are hereby incorporated by this reference in their entireties, and a luminescence quenching type sensor, as described in U.S. Pat. 6,325,978, issued to Labuda et al. on Dec. 4, 2001 (hereinafter "the '978 Patent), the disclosure of which is hereby incorporated herein by this reference in its entirety. A complementary transducer would, of course, act as a pressure transducer and one or both of an infrared sensing type transducer and luminescence excitation and detection transducer.

Figure 7:
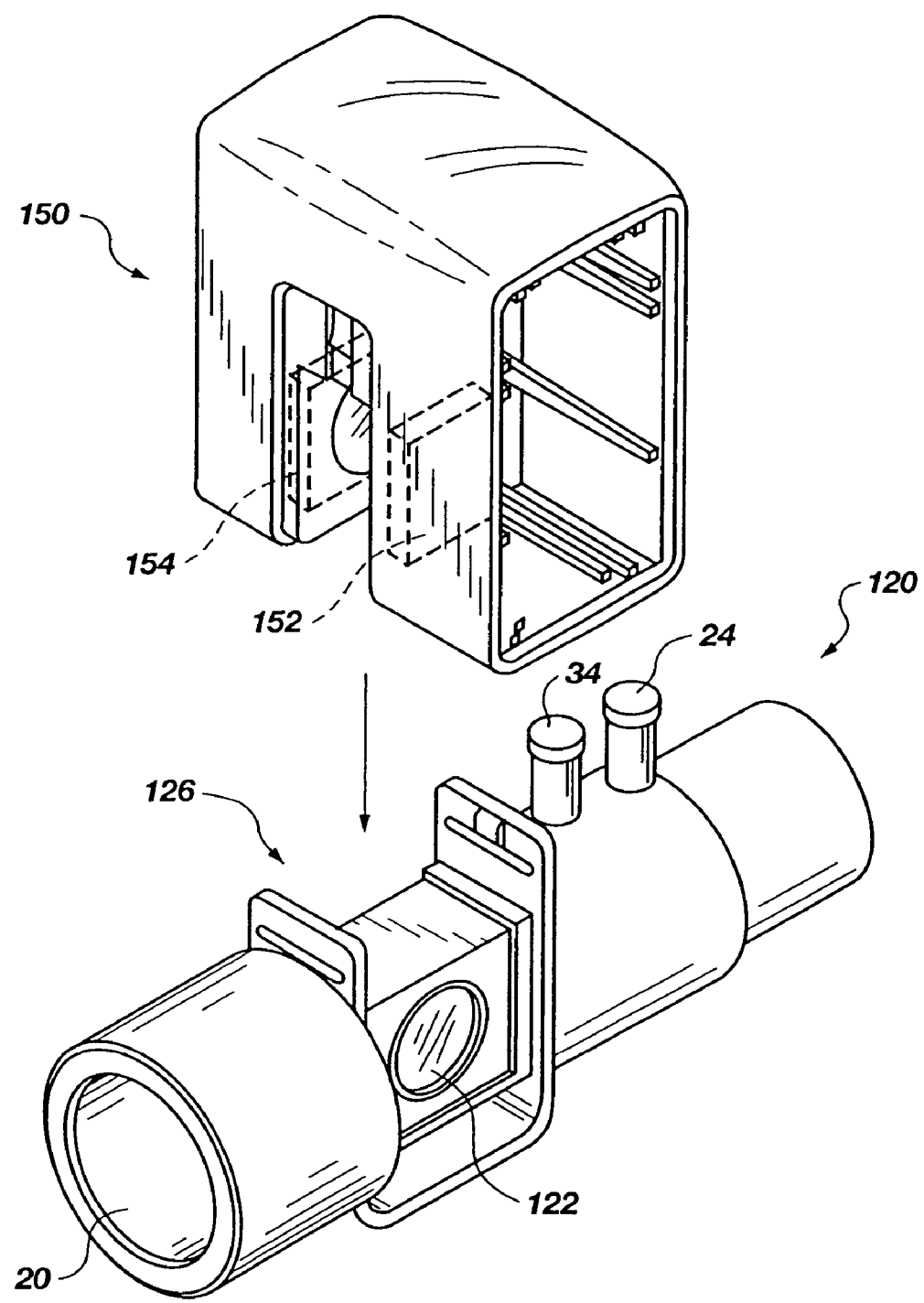
FIG. 7 is a perspective assembly view of an exemplary embodiment of a multi-function airway adapter, including a pressure sensing component, an infrared sensing component, and a complementary infrared sensing type transducer that incorporate teachings of the present invention.

FIG. 7 schematically depicts an example of an assembly including a multi-function airway adapter 120 and a transducer 150 of an infrared type sensor that may be used therewith. Airway adapter 120 has the features of pneumotach 20 described previously herein with reference to FIGS. 2, 3, and 5, to which a complementarily configured portable pressure transducer 50 (FIGS. 4 and 5) may be secured. In addition, airway adapter 120 includes a pair of opposed windows 122, only one of which is shown, which facilitate the transmission of infrared radiation through primary conduit 22 of airway adapter 120 and any gases or vaporized materials therein, as well as the detection of infrared radiation that has not been absorbed by windows 122 or gases or other materials within primary conduit 22. Airway adapter 120 also includes a seating element 126, which is configured to ensure that the complementarily configured transducer 150 seats properly, i.e., in the proper orientation, when airway adapter 120 and transducer 150 are assembled with one another. When properly positioned on airway adapter 120, transducer 150 preferably does not interfere with the assembly of a portable pressure transducer 50 (FIGS. 4 and 5) with airway adapter 120. Transducer 150 may include each of the elements of an infrared monitoring transducer, as described in the '858, '859, and '436 Patents. Among other things, an infrared source 152 and at least one infrared detector 154 may be positioned so as to respectively direct infrared radiation into one window 122 and detect infrared radiation through the other window (not shown). Operation of infrared source 152 and infrared detector 154 may be controlled and monitored, as known in the art, by a processor of a suitable monitoring apparatus (e.g., processor 102 of monitor 100 shown. in FIG. 5) with which infrared source 152 and infrared detector 154 communicate electronically, as known in the art.

Figure 8:
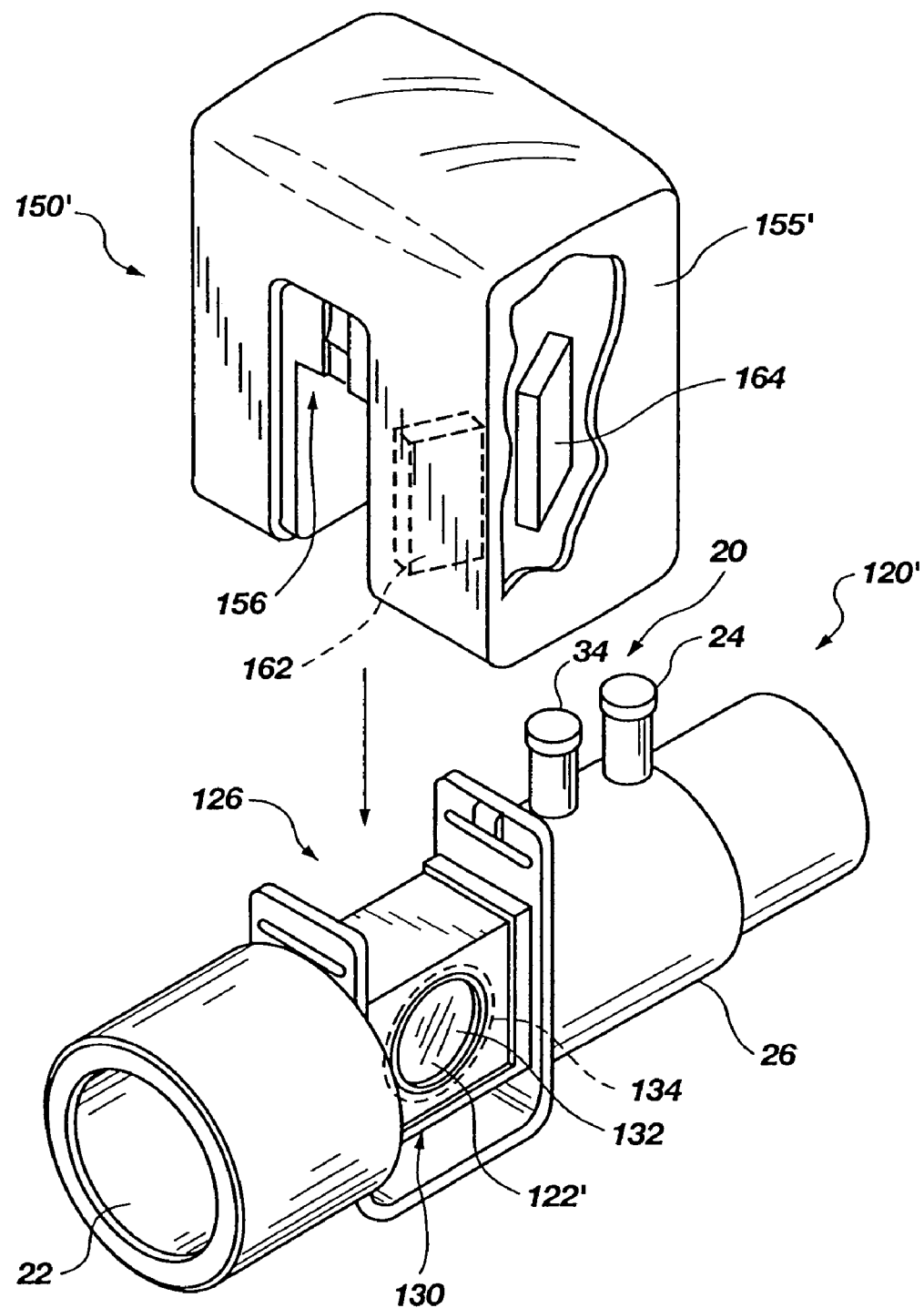
FIG. 8 is a perspective assembly view of another exemplary embodiment of a multi-function airway adapter according to the present invention, which includes a pressure sensing component, a luminescence-quenching type sensing component, and a complementarily configured transducer of a luminescence-quenching type sensor.

Referring now to FIG. 8, an alternative embodiment of multi-function airway adapter 120' and complementary transducer 150' of a luminescence-quenching type sensor are depicted. Airway adapter 120' includes a pneumotach, such as pneumotach 20 described previously herein with reference to FIGS. 2, 3, and 5. Airway adapter 120' also includes a luminescence-quenching portion 130, which facilitates monitoring of one or more substances (e.g., oxygen) in respiratory gases by way of known luminescence quenching techniques, as described in the '978 Patent.

Luminescence-quenching portion 130 of airway adapter 120' includes a quantity of luminescable material 132, which may be carried by a support membrane 134, within a primary conduit 22 of pneumotach 20. The luminescence of luminescable material 132 is quenched to a degree indicative of an amount of an analyzed gas (e.g., oxygen, nitrous oxide, etc.) or vaporized material (e.g., one or more anesthetic agents) in a gas mixture (e.g., respiration of an individual) to which luminescable material 132 is exposed. Airway adapter 120' also includes a window 122' through which at least a portion of luminescable material 132 may be excited into a luminescent state and through which light or other electromagnetic radiation emitted from luminescable material 132 may be detected. Examples of luminescable materials 132 and support membranes 134, as well as their positioning within airway adapter 120' relative to a window 122' thereof, and examples of materials from which window 122' may be formed are more fully described in the '978 Patent.

Transducer 150' includes at least a source 162 of electromagnetic radiation of one or more wavelengths that will excite luminescable material 132 into a luminescent state, as well as a detector 164 for sensing electromagnetic radiation emitted by luminescable material 132. Source 162 and detector 164 are positioned and oriented within a housing 155' of transducer 150' in such a way that both source 162 and detector 164 are oriented toward window 122' of airway adapter 120' and luminescable material 132 within airway adapter 120' when transducer 150' and airway adapter 120' are assembled with one another. The specifics of source 162, detector 164, and other elements of transducer 150', including control and monitoring of their operation by a processor of a suitable monitoring apparatus (e.g., processor 102 of monitor 100 shown in FIG. 5) and transmission of signals from detector 164 to such a processor are more fully described in the '978 Patent.

Airway adapter 120' may also include a seating element 126, which, along with a complementary element or portion 156 of transducer 150', is configured to ensure that appropriate elements of airway adapter 120' and transducer 150', such as window 122' of airway adapter 120' and source 162 and detector 164 of transducer 150' are in adequate alignment with one another upon assembly of airway adapter 120' and transducer 150'. When transducer 150' is properly positioned on airway adapter 120', transducer 150' preferably does not interfere with the assembly or disassembly of portable pressure transducer 50 (FIGS. 4 and 5) with its respective luminescence-quenching portion 130 of airway adapter 120'.

In addition to the material sensing functions of transducers 150 and 150' depicted in FIGS. 7 and 8, respectively, transducers 150 and 150' may be equipped with pressure sensing portions which include the features of a portable pressure transducer of the present invention (e.g., portable pressure transducer 50 depicted in FIGS. 4 and 5).

Once signals that correspond to pressure measurements obtained by use of a pneumotach (e.g., pneumotach 20 shown in FIG. 5) and complementary portable pressure transducer (e.g., portable pressure transducer 50 shown in FIG. 5) of the present invention have been transmitted to a processor of a pressure monitor (e.g., processor 102 of pressure monitor 100 shown in FIG. 5), known techniques and algorithms may be employed to calculate various flow, volume, respiratory mechanics, and other respiratory parameters, as well as measurements of blood flow and blood gases.

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. An airway adapter, comprising:
   a first housing having a first end configured to be coupled to a respiratory conduit and a second end configured to be coupled to the respiratory conduit;
   a primary conduit defined in the first housing and including a flow restricting portion, wherein the primary conduit includes an inlet at the first end of the first housing and an outlet at the second end of the first housing;
   a first pressure port defined in a sidewall of the first housing between the first end and the second end, wherein the first pressure port is in fluid communication with the primary conduit on a first side of the flow restricting portion;
   a second pressure port defined in the sidewall of the first housing, wherein the second pressure port is in fluid communication with the primary conduit on a second side of the flow restricting portion; and
   a pressure transducer coupling portion disposed on the first housing and configured to selectively and removably engage a second housing of a pressure transducer.

2. The airway adapter of claim 1, the first pressure port includes a first opening and the second pressure port includes a second opening, and further comprising first sealing member covering the first opening and a second sealing member covering the second opening.

3. The airway adapter of claim 1, further comprising a first hollow protruding portion extending from the first housing at the first pressure port and a second hollow protruding portion extending from the first housing at the second pressure port.

4. The airway adapter of claim 3, wherein the first hollow protruding portion includes a first piercing portion disposed at an end thereof, and wherein the second hollow protruding portion includes a second piercing portion disposed at an end thereof.

5. The airway adapter of claim 1, wherein the pressure transducer coupling portion defines a seating element that properly orients a complementarily configured transducer responsive to the transducer being coupled to the airway adapter.

6. A pressure transducer comprising:
   (a) a transducer housing;
   (b) a coupling portion disposed on the transducer housing and configured to selectively and removably attach to a pneumotach housing;
   (c) a first pressure sensor disposed in the transducer housing, wherein the first pressure sensor outputs a signal indicative of a pressure monitored by the pressure sensor;
   (d) a first sample conduit that includes (1) a first portion disposed in the transducer housing and coupled to the first pressure sensor and (2) a second portion adapted to cooperate with a first pressure port on a pneumotach responsive to the transducer housing being coupled to such a pneumotach housing; and
   (e) a second sample conduit that includes (1) a first portion disposed in the transducer housing and coupled to the first pressure sensor and (2) a second portion adapted to cooperate with a second pressure port on a pneumotach responsive to the transducer housing being coupled to such a pneumotach housing.

7. The pressure transducer of claim 6, wherein the second portion of the first conduit and the second portion of the second conduit is defined by a portion of the transducer housing.

8. The pressure transducer of claim 7, wherein the portion of the transducer housing defining the second portion of the first conduit and defining the second portion of the second conduit each includes a piercing portion.

9. The pressure transducer of claim 6, wherein the first pressure sensor comprises a differential pressure sensor in communication with the first and the second sample conduits.

10. The pressure transducer of claim 6, further comprising a second pressure sensor including a (1) first portion in communication with at least one of the first sample conduit and the second sample conduit and (2) a second portion in communication with an environment external to the pressure transducer.

11. The pressure transducer of claim 6, wherein the first sampling conduit includes a first opening and the second sampling conduit includes a second opening, and further comprising a first sealing portion covering the first opening and a second sealing portion covering the second opening.

12. The pressure transducer of claim 11, wherein the first sealing portion and the second sealing portion are defined by a common sealing member.

13. The pressure transducer of claim 6, wherein the second portion of the first sample conduit comprises a first piercing member, and wherein the second portion of the second sample conduit comprises a second piercing member.

14. The pressure transducer of claim 6, further comprising (1) a first valve disposed in the first sample conduit and (2) a second valve disposed in the second sample conduit.

15. An airway adapter comprising:
 a first housing having a first end configured to be coupled to a respiratory conduit and a second end configured to be coupled to the respiratory conduit;
 a primary conduit defined in the first housing and including a flow restricting portion;
 a first pressure port defined in the first housing in fluid communication with the primary conduit on a first side of the flow restricting portion;
 a second pressure port defined in the first housing in fluid communication with the primary conduit on a second side of the flow restricting portion; and
 a pressure transducer coupling portion disposed on the first housing and configured to selectively and removably engage a second housing of a pressure transducer, wherein the pressure transducer coupling portion defines a seating element that properly orients a complementarily configured transducer responsive to the transducer being coupled to the airway adapter.

* * * * *